(12) United States Patent
Usher

(10) Patent No.: US 11,607,155 B2
(45) Date of Patent: Mar. 21, 2023

(54) METHOD TO ESTIMATE HEARING IMPAIRMENT COMPENSATION FUNCTION

(71) Applicant: Staton Techiya, LLC, Delray Beach, FL (US)

(72) Inventor: John Usher, Beer (GB)

(73) Assignee: Staton Techiya, LLC, Delray Beach, FL (US)

( * ) Notice: Subject to any disclaimer, the term of this patent is extended or adjusted under 35 U.S.C. 154(b) by 880 days.

(21) Appl. No.: 16/295,900

(22) Filed: Mar. 7, 2019

(65) Prior Publication Data

US 2019/0274595 A1 Sep. 12, 2019

Related U.S. Application Data

(60) Provisional application No. 62/641,332, filed on Mar. 10, 2018.

(51) Int. Cl.
*A61B 5/12* (2006.01)
*A61B 5/00* (2006.01)
*G06F 3/16* (2006.01)
*G10L 25/60* (2013.01)

(52) U.S. Cl.
CPC ............ *A61B 5/12* (2013.01); *A61B 5/6803* (2013.01); *G06F 3/165* (2013.01); *G10L 25/60* (2013.01)

(58) Field of Classification Search
CPC . H04L 1/1628; H04L 1/1896; H04L 41/0213; H04L 43/0835; H04L 47/10; H04L 47/70; H04L 47/724; H04L 47/781; H04L 47/785; H04L 69/324; H04M 1/04; H04N 17/00; H04N 17/004; H04N 19/103; H04N 19/115; H04N 19/61; H04N 19/85; H04N 19/89; H04N 21/44008; H04N 21/6437; H04W 74/08; H04W 84/12
USPC .................................. 381/60, 312; 600/550
See application file for complete search history.

(56) References Cited

U.S. PATENT DOCUMENTS

| | | |
|---|---|---|
| 3,876,843 A | 4/1975 | Moen |
| 4,054,749 A | 10/1977 | Suzuki et al. |
| 4,088,849 A | 5/1978 | Usami et al. |
| 4,947,440 A | 8/1990 | Bateman et al. |
| 5,208,867 A | 5/1993 | Stites, III |

(Continued)

FOREIGN PATENT DOCUMENTS

| | | |
|---|---|---|
| EP | 1519625 | 3/2005 |
| EP | 1519625 A2 | 3/2005 |

(Continued)

OTHER PUBLICATIONS

Olwal, A. and Feiner S. Interaction Techniques Using Prosodic Features of Speech and Audio Localization. Proceedings of IUI 2005 (International Conference on Intelligent User Interfaces), San Diego, CA, Jan. 9-12, 2005, p. 284-286.

(Continued)

*Primary Examiner* — Lun-See Lao
(74) *Attorney, Agent, or Firm* — Akerman LLP; Peter A. Chiabotti

(57) ABSTRACT

At least one exemplary embodiment is directed to a method of generating a hearing impairment compensation function to process audio reproduced by an earphone device. The compensation function includes processing the audio to compensate for frequency sensitivity to improve speech intelligibility.

11 Claims, 5 Drawing Sheets

(56) References Cited

U.S. PATENT DOCUMENTS

| | | |
|---|---|---|
| 5,267,321 A | 11/1993 | Langberg |
| 5,524,056 A | 6/1996 | Killion et al. |
| 5,903,868 A | 5/1999 | Yuen et al. |
| 6,021,207 A | 2/2000 | Puthuff et al. |
| 6,021,325 A | 2/2000 | Hall |
| 6,163,338 A | 12/2000 | Johnson et al. |
| 6,163,508 A | 12/2000 | Kim et al. |
| 6,226,389 B1 | 5/2001 | Lemelson et al. |
| 6,298,323 B1 | 10/2001 | Kaemmerer |
| 6,359,993 B2 | 3/2002 | Brimhall |
| 6,400,652 B1 | 6/2002 | Goldberg et al. |
| 6,415,034 B1 | 7/2002 | Hietanen |
| 6,567,524 B1 | 5/2003 | Svean et al. |
| RE38,351 E | 12/2003 | Iseberg et al. |
| 6,661,901 B1 | 12/2003 | Svean et al. |
| 6,728,385 B2 | 4/2004 | Kvaloy et al. |
| 6,748,238 B1 | 6/2004 | Lau |
| 6,754,359 B1 | 6/2004 | Svean et al. |
| 6,804,638 B2 | 10/2004 | Fiedler |
| 6,804,643 B1 | 10/2004 | Kiss |
| 7,072,482 B2 | 7/2006 | Van Doorn et al. |
| 7,107,109 B1 | 9/2006 | Nathan et al. |
| 7,209,569 B2 | 4/2007 | Boesen |
| 7,430,299 B2 | 9/2008 | Armstrong et al. |
| 7,433,714 B2 | 10/2008 | Howard et al. |
| 7,450,730 B2 | 11/2008 | Bertg et al. |
| 7,477,756 B2 | 1/2009 | Wickstrom et al. |
| 7,562,020 B2 | 6/2009 | Le et al. |
| 7,756,285 B2 | 7/2010 | Sjursen et al. |
| 7,778,434 B2 | 8/2010 | Juneau et al. |
| 7,920,557 B2 | 4/2011 | Moote |
| 7,929,713 B2 | 4/2011 | Victorian |
| 8,014,553 B2 | 9/2011 | Radivojevic et al. |
| 8,116,489 B2 * | 2/2012 | Mejia .................. H04R 25/505 381/95 |
| 8,493,204 B2 | 7/2013 | Wong et al. |
| 8,750,295 B2 | 6/2014 | Liron |
| 9,037,458 B2 | 5/2015 | Park et al. |
| 9,107,016 B2 * | 8/2015 | Shennib ............... H04R 25/70 |
| 9,123,343 B2 | 9/2015 | Kurki-Suonio |
| 9,135,797 B2 | 9/2015 | Couper et al. |
| 9,326,706 B2 * | 5/2016 | Shennib ............... A61B 5/123 |
| 10,455,337 B2 * | 10/2019 | Yoo ..................... A61B 5/123 |
| 10,715,932 B2 * | 7/2020 | Liebich ................ H04R 25/30 |
| 10,887,679 B2 * | 1/2021 | Boesen ................ H04R 1/1041 |
| 2001/0046304 A1 | 11/2001 | Rast |
| 2002/0106091 A1 | 8/2002 | Furst et al. |
| 2002/0118798 A1 | 8/2002 | Langhart et al. |
| 2003/0161097 A1 | 8/2003 | Le et al. |
| 2003/0165246 A1 | 9/2003 | Kvaloy et al. |
| 2004/0042103 A1 | 3/2004 | Mayer |
| 2004/0109668 A1 | 6/2004 | Stuckman |
| 2004/0125965 A1 | 7/2004 | Alberth, Jr. et al. |
| 2004/0190737 A1 | 9/2004 | Kuhnel et al. |
| 2004/0196992 A1 | 10/2004 | Ryan |
| 2004/0203351 A1 | 10/2004 | Shearer et al. |
| 2005/0078838 A1 | 4/2005 | Simon |
| 2005/0123146 A1 | 6/2005 | Voix et al. |
| 2005/0288057 A1 | 12/2005 | Lai et al. |
| 2006/0067551 A1 | 3/2006 | Cartwright et al. |
| 2006/0083395 A1 | 4/2006 | Allen et al. |
| 2006/0092043 A1 | 5/2006 | Lagassey |
| 2006/0195322 A1 | 8/2006 | Broussard et al. |
| 2006/0204014 A1 * | 9/2006 | Iseberg ................ A61B 5/121 381/60 |
| 2007/0043563 A1 | 2/2007 | Comerford et al. |
| 2007/0086600 A1 | 4/2007 | Boesen |
| 2007/0189544 A1 | 8/2007 | Rosenberg |
| 2007/0270988 A1 * | 11/2007 | Goldstein ............. H04R 5/04 381/309 |
| 2007/0291953 A1 | 12/2007 | Ngia et al. |
| 2008/0037801 A1 | 2/2008 | Alves et al. |
| 2008/0165988 A1 | 7/2008 | Terlizzi et al. |
| 2009/0010456 A1 | 1/2009 | Goldstein et al. |
| 2009/0024234 A1 | 1/2009 | Archibald |
| 2010/0061564 A1 | 3/2010 | Clemow et al. |
| 2010/0296668 A1 | 11/2010 | Lee et al. |
| 2011/0096939 A1 | 4/2011 | Ichimura |
| 2011/0264447 A1 | 10/2011 | Visser et al. |
| 2011/0293103 A1 | 12/2011 | Park et al. |
| 2016/0104452 A1 | 4/2016 | Guan et al. |

FOREIGN PATENT DOCUMENTS

| | | |
|---|---|---|
| WO | 2006037156 | 4/2006 |
| WO | 2006037156 A1 | 4/2006 |

OTHER PUBLICATIONS

Bernard Widrow, John R. Glover Jr., John M. McCool, John Kaunitz, Charles S. Williams, Robert H. Hearn, James R. Zeidler, Eugene Dong Jr, and Robert C. Goodlin, Adaptive Noise Cancelling: Principles and Applications, Proceedings of the IEEE, vol. 63, No. 12, Dec. 1975.

Mauro Dentino, John M. McCool, and Bernard Widrow, Adaptive Filtering in the Frequency Domain, Proceedings of the IEEE, vol. 66, No. 12, Dec. 1978.

\* cited by examiner

METHOD TO ESTIMATE HEARING IMPAIRMENT COMPENSATION FUNCTION

CROSS-REFERENCE TO RELATED APPLICATIONS

This application is a non provisional of and claims priority to U.S. Pat. App. No. 62/641,332, filed 10 Mar. 2018, the disclosure of which is incorporated herein by reference in its entirety.

FIELD OF THE INVENTION

The present invention relates in general to methods for modification of audio content and in particular, though not exclusively, for the personalization of audio content using a hearing impairment compensation function.

BACKGROUND OF THE INVENTION

A Hearing Sensitivity Transfer Function (HSTF) can be equated with an equal loudness contour for an individual at the threshold of hearing, which can be obtained with a hearing test. The hearing threshold curve, also called the absolute threshold of hearing (ATH), is the minimum sound level of a pure tone that a given individual can hear with no other sound present. The hearing threshold curve is frequency dependent and can be significantly different for a left and right ear of a given individual and is typically obtained using the presentation of pure sine waves with headphones. The curve shape differs for different individuals due to the resonant properties of the outer ear and hearing sensitivity due to damage within the auditory system, e.g. hair-cell damage in the inner ear.

The HSTF, herein defined, is similarly a frequency dependent curve showing the sound pressure level required to produce a given perceptual loudness level, which is taken as the minimum threshold sound pressure level that can be detected for a given individual. The HSTF is different from the hearing threshold curve in that it is determined using band-pass filtered audio signals, typically music audio signals, with band pass filter sizes of typically ⅓rd octave.

The advantage of using such a methodology, i.e. using music-like stimulus instead of pure sine waves, is that the stimulus in the listening test to acquire the HSTF has a music like quality, such as a musical rhythm and a tonality similar to the original audio that was band-pass filtered. As such, the lengthy listening tests to acquire the HSTF will be more interesting to listen to than the lengthy listening tests used to acquire a hearing threshold curve, as the individual can select a piece of music from a personalized playlist or music audio library.

An HSTF can be used with a hearing enhancement system worn by a user to increase the speech intelligibility of the user for presented human speech. A hearing enhancement system can be generally classified as a hearing aid, for instance a hearing aid prescribed for hearing impairment and for Personal Sound Amplification Products (PSAPs) that do general not require a medical prescription.

BRIEF DESCRIPTION OF THE DRAWINGS

Exemplary embodiments of present invention will become more fully understood from the detailed description and the accompanying drawings, wherein.

DETAILED DESCRIPTION OF EXEMPLARY EMBODIMENTS

Figure 1:
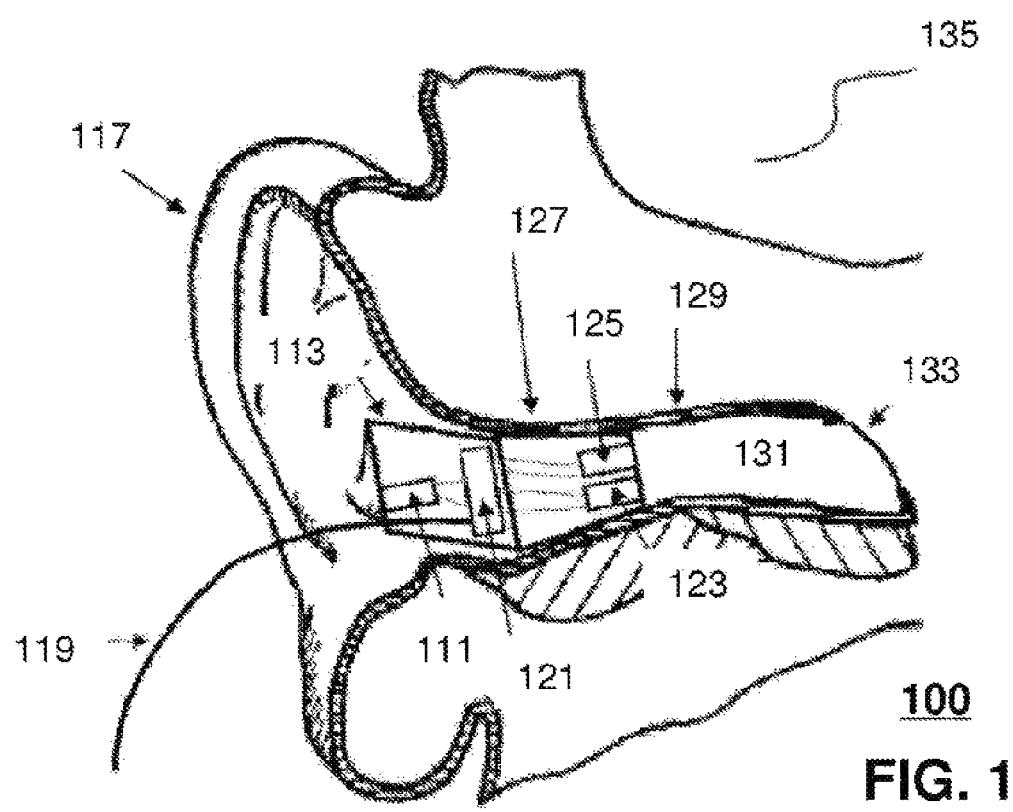
FIG. 1 shows a diagram of an earpiece/earphone in accordance with an exemplary embodiment.

The following description of exemplary embodiment(s) is merely illustrative in nature and is in no way intended to limit the invention, its application, or uses.

Exemplary embodiments are directed to or can be operatively used on various wired or wireless audio devices (e.g., hearing aids, ear monitors, earbuds, headphones, ear terminal, behind the ear devices or other acoustic devices as known by one of ordinary skill, and equivalents). For example, the earpieces can be without transducers (for a noise attenuation application in a hearing protective earplug) or one or more transducers (e.g. ambient sound microphone (ASM), ear canal microphone (ECM), ear canal receiver (ECR)) for monitoring/providing sound. In all the examples illustrated and discussed herein, any specific values should be interpreted to be illustrative only and non-limiting. Thus, other examples of the exemplary embodiments could have different values.

Processes, techniques, apparatus, and materials as known by one of ordinary skill in the art may not be discussed in detail but are intended to be part of the enabling description where appropriate. For example, specific materials may not be listed for achieving each of the targeted properties discussed, however one of ordinary skill would be able, without undo experimentation, to determine the materials needed given the enabling disclosure herein.

Notice that similar reference numerals and letters refer to similar items in the following figures, and thus once an item is defined in one figure, it may not be discussed or further defined in the following figures. Processes, techniques, apparatus, and materials as known by one of ordinary skill in the relevant art may not be discussed in detail but are intended to be part of the enabling description where appropriate.

An Inverse Hearing Sensitivity Transfer Function can be used to process an audio content signal, providing the user/system with an enhanced and improved listening experience optimized for their anthropometrical measurements, anatomy relevant to audition, playback hardware, and personal preferences.

Current hearing enhancement fitting systems and methods to acquire an HSTF are generally complex, relying on specialized instruments for operation by hearing professionals in clinical settings, or using dedicated hardware if the test is self-administered. For example, a HSTF measurement system can comprise an audiometer for conducting a hearing evaluation, a software program for computing prescriptive formulae and corresponding fitting parameters, a hearing aid programming instrument to program the computed fitting parameters, a real ear measurement for in-situ evaluation of the hearing aid, a hearing aid analyzer, sound isolation chamber, calibrated microphones.

Characterization and verification of a HSTF is generally conducted by presenting acoustic stimuli (i.e. reproducing an audio signal) with a loudspeaker of a hearing device, such as a loudspeaker or earphone. The hearing aid is often worn in the ear (in-situ) during the fitting process. The hearing aid may also need to be placed in a test chamber for characterization by a hearing aid analyzer.

The acoustic stimulus used for HSTF acquisition generally uses pure audio tones. One non-limiting example of the present invention presents band-passed music audio (presented stimuli), with the music selection being chosen by the user. This provides an advantage over extant tone-based methods in that the hearing test will be subjectively more enjoyable for the user and more appealing, with the added benefit of supporting marketing slogans such as "test your ears using your own music."

One exemplary embodiment of the current invention introduces a method using an earphone device with at least one ear canal microphone configured to measure the sound pressure level of the presented stimuli. The earphone includes a sound isolating component, so the ambient sound field is not required to be as low as with conventional hearing tests. Thus, the current invention provides advantages over extant HSTF acquisition methods in that the hearing tests can be undertaken in more typical every day sound environments using earphone devices that the user can then use for music reproduction, voice communication, and ambient sound listening with an enhanced and improved intelligibility.

Hearing aid consumers are generally asked to return to the dispensing office to adjust following real-life listening experiences with the hearing device. When simulated "real life" sounds are employed for hearing aid evaluation, calibration of the real-life input sounds at the microphone of the hearing aid is generally required, involving probe tube measurements, or a sound level meter (SLM). Regardless of the method used, conventional fitting generally requires clinical settings to employ specialized instruments for administration by trained hearing professionals. Throughout this application, the term "consumer" generally refers to a person being fitted with a hearing device, thus may be interchangeable with any of the terms "user," "person," "client," "hearing impaired," etc. Furthermore, the term "hearing device" is herein used to refer to all types of hearing enhancement devices, including hearing aids prescribed for hearing impairment and personal sound amplification products (PSAP) generally not requiring a prescription or a medical waiver or any sound isolation earphone with an ear canal microphone, ambient sound microphone and a speaker.

According to one aspect of the invention, a method is provided to determine a hearing impairment compensation function, which is generated from a Hearing Sensitivity Transfer Function (HSTF), to process audio reproduced by an earphone device. The hearing impairment compensation function can approximate the inverse of the HSTF: for instance, a 3-dB dip in the HSTF (relative to a reference normal hearing curve) would correspond to a 3-dB boost in the inverse HSTF curve.

A method is provided to acquire the HSTF using a portable computing device. In one embodiment, the portable computing device includes an audio processing component coupled with an audio output device and a user input interface, and operatively coupled to an earphone device via either a wired or wireless audio connection. The method (called an "HSTF test" or "hearing test") can be performed by carrying out the following operations: —receiving a selected audio content signal at the audio input device, for instant music audio selected from a user's media liberty or remote music streaming server; determining if the frequency content of the received audio signal is suitable for conducting an HSTF test; filtering the received audio signal using at least one of a group of filters, each with separate center frequencies, to split the input audio data into a number of frequency bands to generate at least one filtered signals; determining if ambient sound conditions are suitable for an HSTF test; determining the sensitivity of a presentation loudspeaker; presenting each of the filtered signals to a user with the earphone at a first sound pressure level and for each presentation: determining the minimum presentation level at which the user can hear the presented filtered signal; and generate a frequency dependent HSTF, a sound pressure level (SPL) value for each center frequency band, where the value is equal to the audible loudness level for that frequency.

In another embodiment of the described invention, the audible loudness level is determined using standard audiometric tests known to one skilled in the art, such as the Modified Hughson-Westlake method, or the Bekesy audiometry test.

At least one further embodiment is directed to a method of calibrating the earphone for administering the HSTF test. The method uses an ear canal microphone signal from the earphone to measure the frequency dependent level in response to an emitted test signal.

At least one further embodiment is directed to a method to determine if ambient sound conditions are suitable for an HSTF test. The method uses a microphone proximal to the user's ear, such as an ambient sound microphone or ear canal microphone on the earphone that is used to administer the test.

At least one further embodiment is directed to a method to determine if the earphone is fitted correctly in the ear prior to conducting an HSTF test. The method uses an ear canal microphone to test the ear seal integrity produced by the earphone.

At least one exemplary embodiment of the invention is directed to an earpiece for speech intelligibility enhancement. Reference is made to FIG. 1 in which an earpiece device, indicated as earpiece 100, is constructed and operates in accordance with at least one exemplary embodiment of the invention. As illustrated, earpiece 100 depicts an electroacoustic assembly 113 for an in-the-ear acoustic assembly and wire 119 (if wired), where a portion of the assembly 113 is typically placed in the ear canal 131 of a user 135. The earpiece 100 can be an in the ear earpiece, or other suitable earpiece type. The earpiece 100 can be partially or fully occluded in the ear canal 131.

Earpiece 100 includes an Ambient Sound Microphone (ASM) 111 to capture ambient sound, an Ear Canal Receiver (loudspeaker) 125 to deliver audio to an ear canal 131, and an Ear Canal Microphone 123 to detect sound pressure closer to the tympanic membrane 133 compare to that measured by the ASM, an ear seal mechanism 127 to create an occluded space in the ear canal 129.

The earpiece 100 can partially or fully occlude the ear canal 131 to provide various degrees of acoustic isolation with an ear seal. The ear seal 127 is typically made from a foam, soft rubber or balloon material and serves to reduce the transmission of ambient sound into the occluded ear canal.

The microphones 123, 111, and loudspeaker 123, are operatively connected to a digital signal processing device 121, a DSP. The DSP can contain a wireless transceiver to connect with a portable computing device, such as a mobile phone, and optionally connected to another earphone via wire 119.

Figure 2:
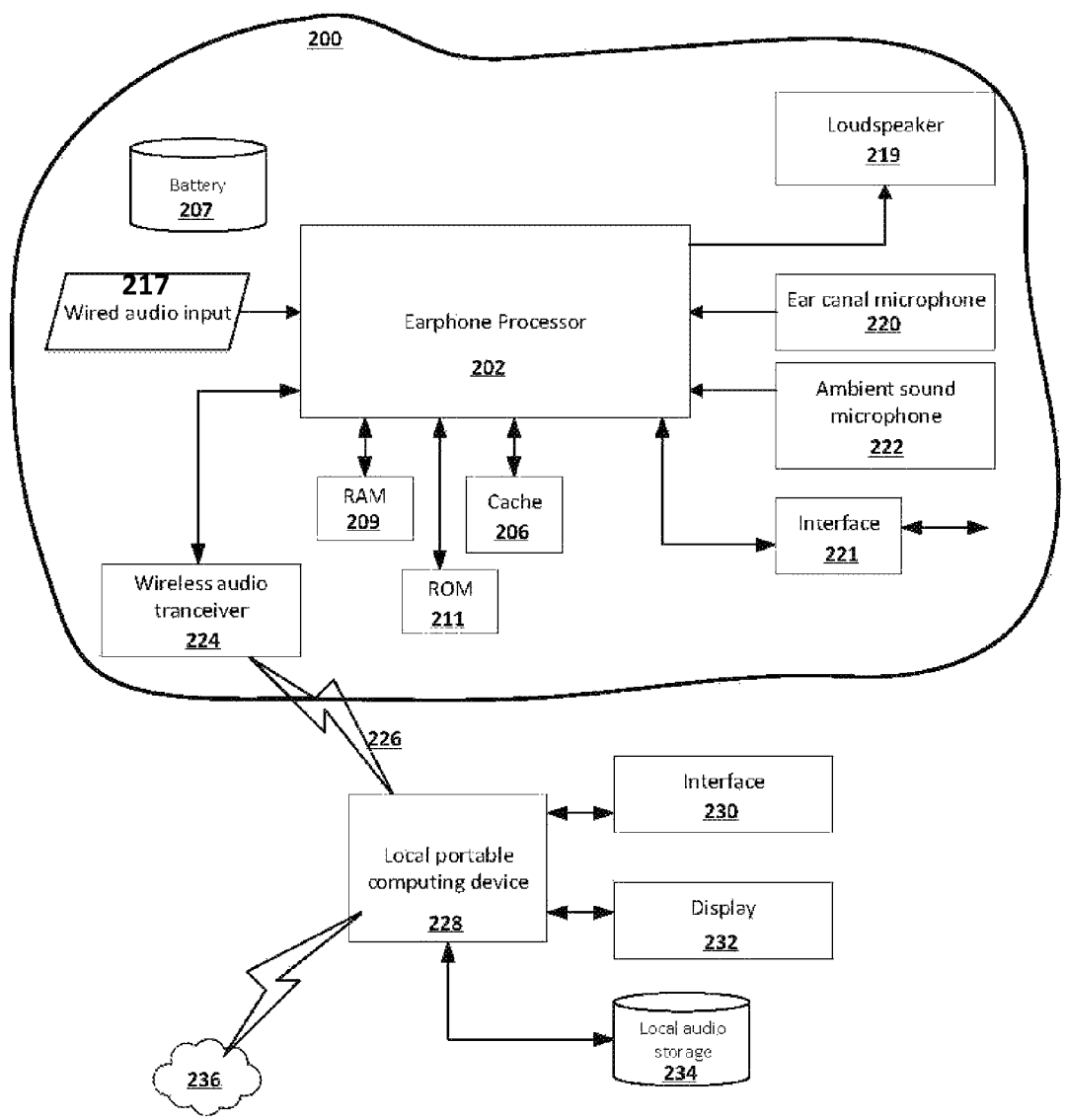
FIG. 2 shows a block diagram of an earpiece system in accordance with the described embodiments.

FIG. 2 is a block diagram of an electronic earphone device suitable for use with at least one of the described embodiments. The electronic device 200 illustrates circuitry of a representative computing device. The electronic device 200 includes a processor 202 that pertains to a Digital Signal Processor (DSP) device or microprocessor or controller for controlling the overall operation of the electronic device 200. For example, processor 202 can be used to receive a wireless 224 or wired 217 audio input signals. The electronic device 200 can also include a cache 206. The cache 206 is, for example, Random Access Memory (RAM) provided by semiconductor memory. The relative access time to the cache 206 is substantially shorter than for the system RAM 209.

The electronic device 200 is powered by a battery 207. The electronic device 200 can also include the RAM 209 and a Read-Only Memory (ROM) 211. The ROM 211 can store programs, utilities or processes to be executed in a non-volatile manner.

The speaker 219 is an ear canal loudspeaker, also often referred to as a receiver. Microphone 220 can be used to detect audible sound in the ear canal (ear canal microphone). A second microphone 222 can be used to detect audible sound in the ambient environment (ambient sound microphone).

An optional interface 221 on the earphone device 200 can be used for user input, such as a capacitive touch sensor.

A wireless audio and data transceiver unit 224 connects with a computing device 228 (e.g., a local portable computing device). The wireless connection 226 can be any electromagnetic connection, for example via Bluetooth or Wifi or magnetic induction, and transmits audio and control data. The local portable computing device 228 can be a mobile phone, tablet, television, gaming hardware unit or other similar hardware devices.

The local portable computing device 228 utilizes a user interface 230 and display 232, such as a touch screen or buttons, and can be connected to the cloud 236 to receive and stream audio. Alternatively, audio can be replayed to the earphone device 200 from storage 234 on the computing device 228.

Figure 3:
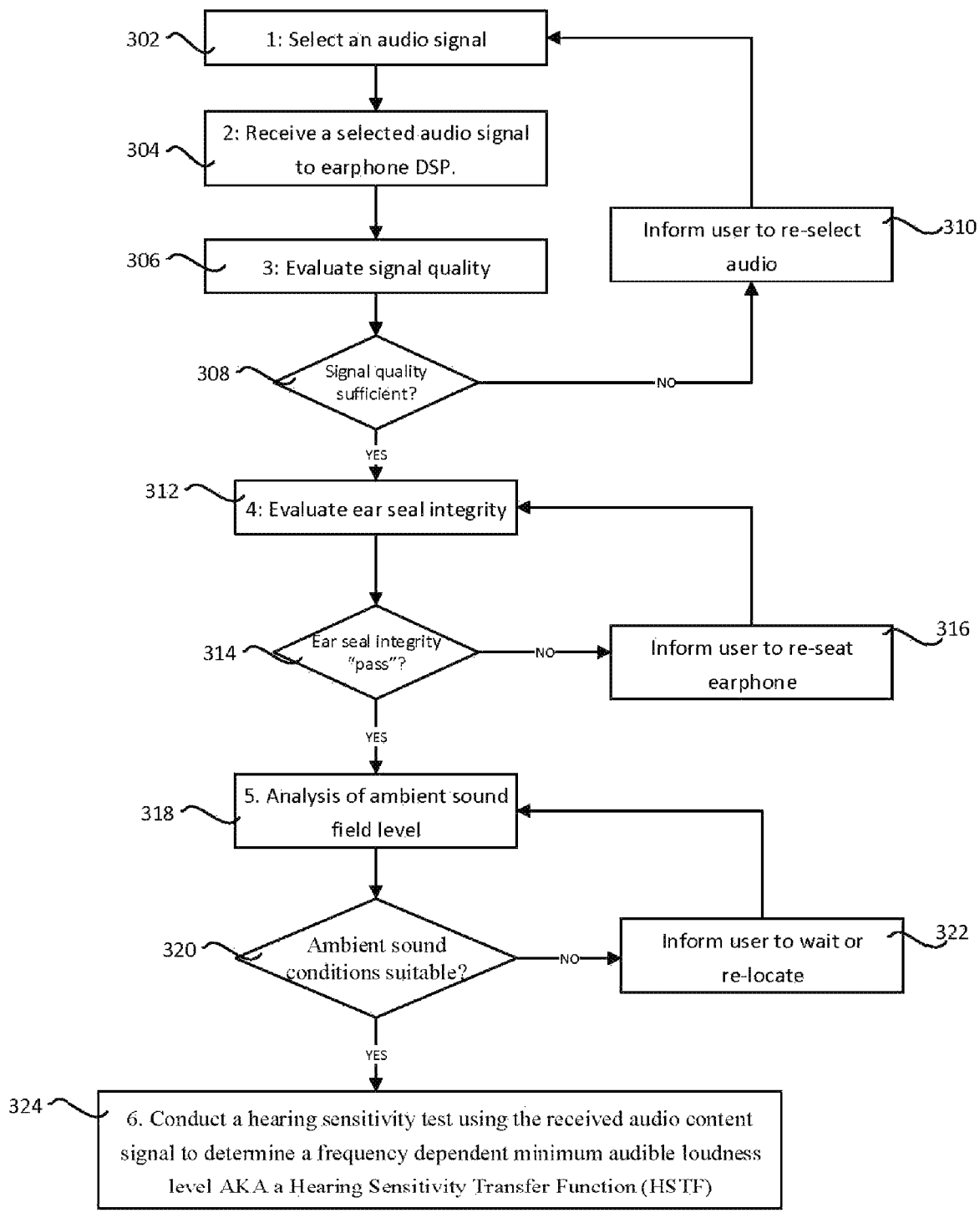
FIG. 3 shows a flow chart detailing an exemplary method for obtaining an HSTF.

FIG. 3 shows a flow chart for acquiring a Hearing Sensitivity Transfer Function (HSTF) for a user comprising the following exemplary steps:

Step 1, 302: Selecting an audio signal: The audio signal is typically music audio stored on a portable computing device communicatively coupled with the earphone device via a wired or wireless audio means (e.g. Bluetooth). Alternatively, the audio signal is stored on a remote web-based server in "the cloud" 236 and is streamed to the portable computing device 228 via wireless means, e.g. via Wi-Fi or a wireless telephone data link. The user can manually select the audio file to be reproduced via a graphical user interface 230, 232 on the portable computing device 228.

Step 2, 304: Sending the selected audio signal to the earphone DSP 202. The audio signal is directed to the earphone DSP 202 via wired or wireless 224 audio means (such as Bluetooth audio).

Step 3, 306: Determining the quality of the received audio content. In the preferred embodiment, the signal quality is determined according to two factors: spectral power and dynamic range. The first quality, spectral power, is an evaluation of how much frequency content there is: with the "pass" criteria generally defined as being sufficient spectral energy for the frequency region over which the HSTF is measured. In one exemplary embodiment, this test is accomplished by measuring the 1/Nth octave band averaged power spectral density (PSD) of a portion of the received audio signal between a lower frequency range fL and upper frequency range fH, and comparing each of the N PSD levels with a set of reference threshold levels, and if at least one of the PSD levels is less than a corresponding reference threshold level, then it is determined that the frequency content of the received audio signal is NOT suitable for conducting an HSTF test, for example a non-limiting example uses a threshold value of PSD=−17 dB, where 0 dB would correspond to the level of a signal of full-scale (i.e. 1.0 Volts). In such a "low quality signal" case, the user is informed 310 to select a different audio input signal. In the preferred embodiment, the ⅓rd octave band is measured (i.e. N=6) between fL=200 Hz to fH=8 kHz. Such a process of informing the user can be via an audio message generated by the earphone processor 202 and reproduced with the earphone loudspeaker 219. If NOT suitable, the user can then also select a pre-saved default audio signal that satisfies the threshold conditions.

The second quality evaluation relates to estimating the dynamic range within each 1/Nth octave band and ensuring that the dynamic range is less than a predetermined amount, which in one exemplary embodiment is set to 20 dB. The dynamic range is defined as the average difference between a short-term level estimate and a long-term level estimate. In a non-limiting example, the short-term level estimate is defined as a running average level within a 100 ms window, and the long-term level is averaged over a 5 second window.

For the HSTF test to be administered using the selected audio, at least one of the first and second quality evaluation criteria must be satisfied.

Step 4, 312: Determining if the earphone used for administering the HSTF test is correctly fitted (sealed) by an analysis of the earphone ear seal (this method is described in FIG. 5). If the ear seal is determined not to be a good fit 314, then the user is informed 316 that the ear seal test is not optimal and prompted to adjust that earphone to attain a good seal, and the ear seal test is repeated.

Step 5, 318: Determining if ambient sound conditions are suitable for an HSTF test. In one exemplary embodiment, this is accomplished by measuring the frequency dependent ambient sound pressure level using the earphone ambient microphone or microphone operatively attached to the local portable computing device. The measured frequency dependent ambient sound pressure level curve (measured SPL vs. freq.) is compared to a reference frequency dependent ambient sound pressure level curve (reference SPL vs. freq.), and if the measured curve is at any point GREATER (measured SPL>reference SPL) than the reference curve for any frequency value, then the ambient sound conditions are determined to not be suitable. In such an unsuitable case, the user is informed 322 that they should re-locate to a quieter ambient environment.

Step 6, 324: Conduct a hearing sensitivity test using the received audio content signal to determine a frequency dependent minimum audible loudness level. This method is described in FIG. 4.

In another aspect of the described embodiment, the audible loudness level is determined using standard audiometric tests known to one skilled in the art, such as the Modified Hughson-Westlake method.

The user responds when they can hear the presented audio via a display input terminal on the mobile computing device 228 that is operatively coupled to the earphone DSP 202.

In another embodiment, the user responds when they can hear the presented audio for example by the user touching the earphone device to signify when the test signal is heard.

The HSTF curve can be updated by averaging multiple HSTF curves generated using prior HSTF tests, and where the prior HSTF tests may be undertaken using different presentation audio stimuli.

Figure 4:
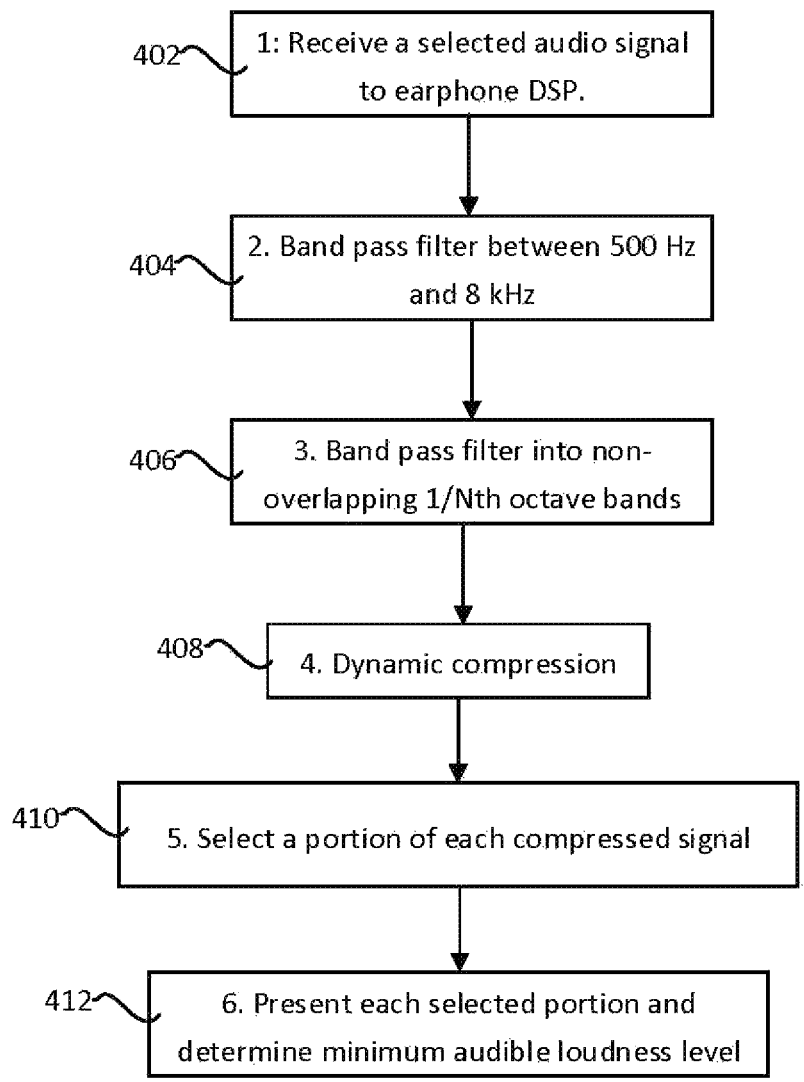
FIG. 4 shows a detailed exemplary method to generate a frequency dependent HSTF.

FIG. 4 shows a detailed exemplary method to generate a frequency dependent HSTF and comprises the steps of:

402 Receiving a selected audio signal to the earphone DSP.

404 Band-pass filtering the selected audio signal between an upper and lower cut-off frequency, which in the preferred embodiment is between 200 Hz and 8 kHz.

406 Filtering the signal from step 2 signal using multiple (X) band-pass filters, each with separate center frequencies, and with non-overlapping frequency content between an upper cut-off frequency of fH and a lower cut-off frequency fL. In the preferred embodiment, the bandwidth of each frequency band is 1/Nth octave (where N=3 in the preferred embodiment), with overall frequency content between 500 Hz and 8 kHz. The number of frequency bands for half octave filtering is therefore equal to: $N*\ln(8000/500)/\ln(2) = 12\frac{1}{3}$rd octave bands.

This generates X (i.e. in the preferred embodiment, 12) new filtered signals. Suitable filters for such band pass filtering can be FIR filters, for instance a gammatone filter, or using cascaded biquad filters. The former has the advantage of less stop-band ripple and linear phase in the pass-band, but at the expense of increased computational complexity. In another embodiment, the band pass filters approximate the size of an auditory band.

The filtered signals are then processed with a dynamic compressor/expander 408 (also known as a compander, but more generally known as a compressor). As familiar to one skilled in the art, the dynamic compressor reduces the dynamic range of the filtered audio signals: i.e. quiet portions of audio are boosted, and loud portions are attenuated. In the preferred embodiment, a simple compressor only function is applied, with a gain ratio of 2:1, i.e. the output compressed signal level is half that of the input level. The purpose of this dynamic compression stage is to enable the minimum audible SPL for each filtered signal to be detected quicker, as in music audio there may be significant time periods where the narrow-band frequency content fluctuates.

Selecting a portion 410 of each of the filtered and compressed signals to a user at a measured sound pressure level and for each presentation. In one exemplary embodiment, the audio selection is undertaken by analyzing the compressed and filtered signal to find a time period, (e.g. 10 second period) of audio with substantial energy, where "substantial energy" is defined as having an RMS mean level greater than a threshold value.

Presenting 412 the selected portion of each of the filtered and compressed signals to a user via earphone loudspeaker 219 at a measured sound pressure level and for each presentation to determine a minimum audible loudness level, i.e. the minimum presentation sound pressure level at which the user can hear each of the presented filtered signal. The sound pressure level is measured using ear canal microphone 220.

A frequency dependent HSTF curve is then generated by aggregating each of the frequency dependent minimum SPLs.

Figure 5:
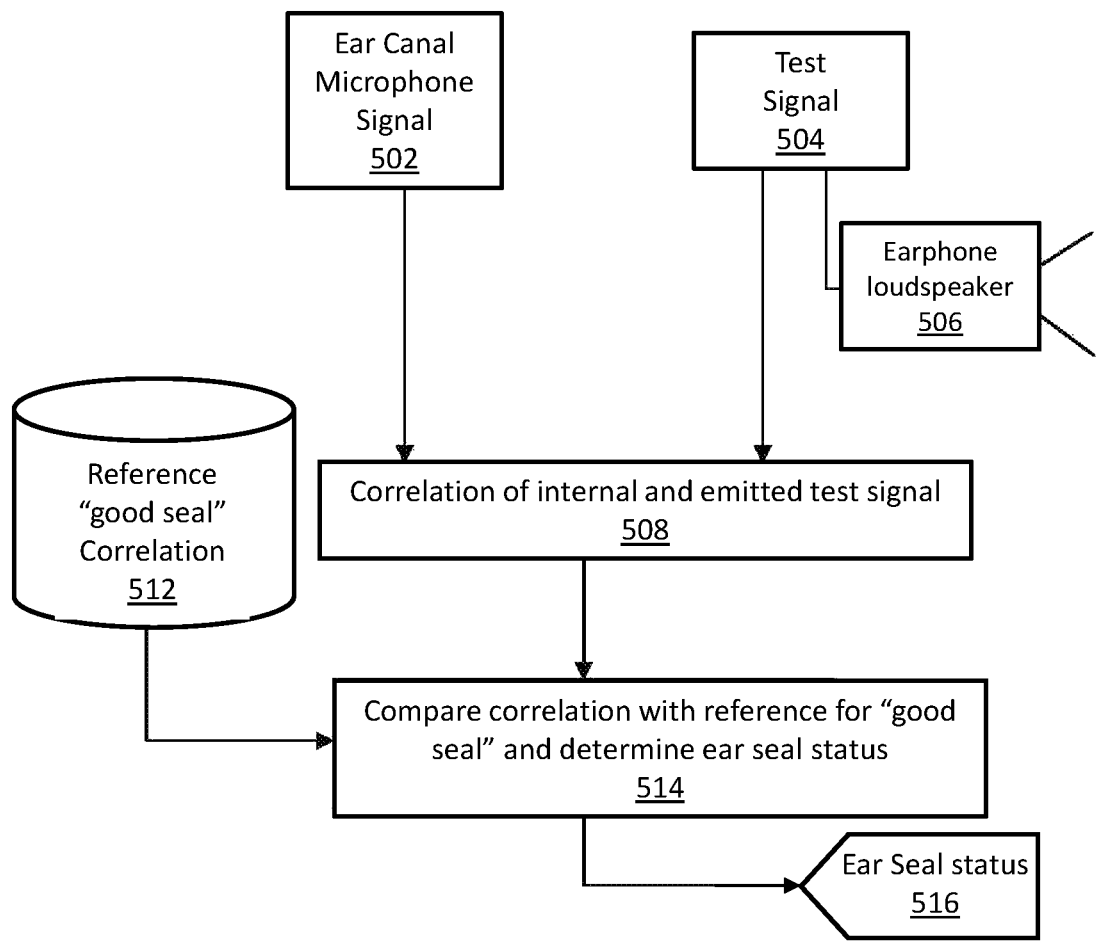
FIG. 5 shows a flow chart detailing an exemplary method to determine if the ear seal is sufficient to conduct an HSTF test.

FIG. 5 shows a flow chart detailing an exemplary method to determine if the ear seal of an earphone is sufficient to conduct an HSTF test.

In at least one embodiment, the method to determine if the earphone used for administering the HSTF test is correctly fitted comprises the steps of:

Step 502. Emitting a test signal with earphone loudspeaker 506, located within a left or right, or both left and right ear(s) of a user. In one exemplary embodiment, the emitted test signal is a 5 second chirp signal (i.e. exponential swept sine wave signal) between 30 Hz and 60 Hz. The signal can be generated using earphone processor 202.

Step 508. Correlating an ear canal microphone signal in the left, right or both left and right ear(s) of the user with the emitted test signal to give a measured average cross-correlation magnitude.

Step 514. Comparing the measured average cross-correlation magnitude with a threshold correlation value 512 to determine ear seal integrity. In one exemplary embodiment, the comparison is a ratio of the measured average cross-correlation magnitude divided by a reference scaler value, where the reference scaler value is the measured average cross-correlation magnitude for a known good ear seal. In such an exemplary embodiment, if the ratio value is greater than unity, then the seal integrity is determined to be "good", i.e. "pass", and "bad" i.e. "fail" otherwise.

If the determined seal integrity is a "fail", the user is informed 516 that the ear seal is not good and to re-seat the earphone sealing unit in the ear canal and repeat the ear seal test. The user can be informed by a visual display message on the operatively connected mobile computing device or audio notification.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used, the intended meaning is "substantially orthogonal" and "substantially perpendicular" respectively. Additionally, although specific numbers may be quoted in the claims, it is intended that a number close to the one stated is also within the intended scope, i.e. any stated number (e.g., 20 mils) should be interpreted to be "about" the value of the stated number (e.g., about 20 mils).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A method of performing a Hearing Sensitivity Transfer Function (HSTF) test for a user comprising the steps of:
   receiving an audio signal, referred to as the received audio signal;
   determining if the quality of the received audio signal is suitable for conducting an HSTF test;
   determining if the earphone used for administering the HSTF test is correctly fitted;
   determining if ambient sound conditions are suitable for an HSTF test; and
   generating a frequency dependent HSTF, where the frequency dependent HSFT is a sound pressure level (SPL) value for each center frequency band, where the value is equal to the audible loudness level for that frequency.

2. The method of claim 1, wherein the step to determine if the quality of the received audio signal is suitable for conducting an HSTF test comprises at least one of the following steps to determine a Power Spectral Density (PSD) quality and a dynamic range quality:

for a chosen N value, the 1/Nth octave band averaged PSD of the received audio signal is calculated between a lower frequency range fL and upper frequency range fH to give N new PSD levels, where the N new PSD levels are compared with a reference curve of N levels and if any of the N new PSD are less than the corresponding PSD values on the reference curve, then the PSD quality of the received audio signal is determined to be insufficient; and a dynamic range quality is determined by estimating the dynamic range of the PSD of the received audio signal, where the dynamic range is defined as the average difference between a short-term level estimate and a long term level estimate, where the short-term level estimate is defined as a running average PSD level within a 100 ms window, and the long-term level is averaged PSD over a 5 second window, where if the dynamic range is greater than a predetermined value, then the dynamic range quality is determined to be insufficient.

3. The method of claim 1, wherein the step to generate a frequency dependent HSTF comprises the steps of:

filtering the received audio signal using X band-pass filters, each with separate center frequency, and with non-overlapping frequency content, to split the received audio signal into X new filtered signals;

applying dynamic compression to the filtered signals creating a filtered and compressed signal;

select a portion of the filtered and compressed signal;

presenting the selected portion to a left or right ear of a user via a loudspeaker in an earphone and determining the audible loudness level for each filtered signal creating frequency dependent audible loudness levels; and generating a frequency dependent HSTF curve by aggregating each of the frequency dependent audible loudness levels.

4. The method of claim 1, wherein the received audio signal is an audio file received from a wired or wirelessly connected mobile computing device, and the audio file is selected from a list of files by a user using a graphical display on the mobile computing device.

5. The method of claim 1, wherein the received audio signal is a streamed portion of an audio file from a wired or wirelessly connected mobile computing device.

6. The method of claim 1, wherein the method of determining if ambient sound conditions are suitable for an HSTF test comprises:

estimating the frequency weighted sound pressure level in the ear canal of the user;

comparing this estimated level with a reference level; and if the estimated level is less than the reference level, the HSTF test is not conducted.

7. The method of claim 1, wherein to calculate the absolute ear canal pressure level, a sensitivity of an earphone loudspeaker is determined by reproducing a test audio signal from the loudspeaker and measuring the acoustic level of the loudspeaker signal using a microphone located proximal to the loudspeaker.

8. The method of claim 1, wherein the minimum presentation level at which the user can hear the presented signal is obtained using a graphical user interface on a mobile computing device as an input device to allow a user to signify when the test signal is heard.

9. The method of claim 1, wherein the minimum presentation level at which the user can hear the presented filtered signal is obtained by the user touching an earphone device to signify when the test signal is heard.

10. The method of claim 1, wherein the HSTF curve is generated by averaging multiple HSTF curves generated using multiple HSTF tests.

11. The method of claim 1, wherein the method to determine if the earphone used for administering the HSTF test is correctly fitted comprises the steps of:

emitting a test signal into the earphone;

simultaneously cross-correlating an ear canal microphone signal with the emitted test signal;

comparing the result of the cross-correlation with a threshold correlation value to determine ear seal integrity; and informing the user that the ear seal is not good if the cross-correlation value is significantly different from the threshold correlation value.

* * * * *